US005762939A

United States Patent [19]

Smith et al.

[11] Patent Number: 5,762,939

[45] Date of Patent: Jun. 9, 1998

[54] METHOD FOR PRODUCING INFLUENZA HEMAGGLUTININ MULTIVALENT VACCINES USING BACULOVIRUS

[75] Inventors: Gale Eugene Smith, Middlefield; Franklin Volvovitz, New Haven; Bethanie Eident Wilkinson, Middletown; Craig Stanway Hackett, Wallingford, all of Conn.

[73] Assignee: MG-PMC, LLC, Swiftwater, Pa.

[21] Appl. No.: 120,607

[22] Filed: Sep. 13, 1993

[51] Int. Cl.[6] .......................... A61K 39/145; C07K 14/11

[52] U.S. Cl. .................................... 424/210.1; 424/209.1; 424/278.1; 424/280.1; 424/816; 530/396

[58] Field of Search .................................... 424/89, 210.1, 424/278.1, 280.1, 816, 209.1; 530/396

[56] References Cited

U.S. PATENT DOCUMENTS

| | | |
|---|---|---|
| 4,289,690 | 9/1981 | Pestka et al. . |
| 4,659,669 | 4/1987 | Kleid et al. . |
| 4,752,473 | 6/1988 | Nayak et al. . |
| 4,920,213 | 4/1990 | Dole et al. . |

OTHER PUBLICATIONS

Clements, "Influenza Vaccines", in Vaccines New Approaches to Immunological Problems, Ed. R.W. Ellis pp. 129–150.

Pennock et al. Mol. Cell Biology 4(3):399–406 1984.

Carr, C.M., et al., "A Spring-loaded Mechanism for the Conformational Change of Influenza Hemagglutinin", *Cell* 73:823–832 (May 1993).

Davis, A.R., et al, "Construction and characterization of a bacterial clone containing the hemagglutinin gene of the WSN strain (HON1) of influenza virus", *Gene*, 10:205–218 (1980).

Eldridge, J.H., et al., "Biodegradable Microspheres: Vaccine Delivery System for Oral Immunization", *Current Topics in Microbiology and Immunology*, 146:59–66 (1989).

Goodman-Snitkoff, G., et al., "Role of Intrastructural/Intermolecular Help in Immunization With Peptide-Phospholipid Complexes", *J. Immunol.*, 147:410–415 (1991).

Harding, C.V. and H.J. Geuze, "Antigen processing and intracellular traffic of antigens and MHC molecules", *Current Opinion in Cell Biology*, 5:596–605 (Aug. 1993).

Johansson, B.E., et al, "Purified Influenza Virus Hemagglutinin and Neuraminidase Are Equivalent in Stimulation of Antibody Response but Induce Contrasting Types of Immunity to Infection", *J. Virology*, 63:1239–1246 (1989).

Kreuter, J., "Nanoparticles—Preparation and Applications" in *Microcapsules and Nanoparticles in Medicine and Pharmacology*, M. Donbrow, ed., CRC Press, Boca Raton, FL, pp. 125–148 (1992).

Maniatis, T., et al., "Large-Scale Isolation of Plasmid DNA", *Molecular Cloning: A Laboratory Manual*, Cold Spring Harbor Lab., Cold Spring, N.Y., pp. 86–96 and 366–367 (1982).

Miller, M.D., et al., "Vaccination of Rhesus Monkeys with Synthetic Peptide in a Fusogenic Proteoliposome Elicits Simian Immunodeficiency Virus-specific $CD8^+$ Cytotoxic T Lymphocytes", *J. Exp. Med.*, 176:1739–1744 (1992).

Murphy, B.R. and R.G. Webster, "Influenza Viruses", in *Fields Virology, Second Edition*, Fields,B.N., et al., eds., Raven Press, New York, pp. 1179–1239 (1990).

Murphy, B.R. and R.G. Webster, "Orthomuxoviruses", in *Fields Virology, Second Edition*, Fields, B.N., et al., eds., Raven Press, New York, pp. 1091–1152 (1990).

Ogra, P.L., et al., "Clinical and Immunologic Evaluation of Neuraminidase-Specific Influenza A Virus Vaccine in Humans", *J. Infect. Dis.*, 135:499–506 (1977).

Powers, D.C., et al., "Effect of Age on Cytotoxic T Lymphocyte Memory as well as Serum and Local Antibody Responses Elicited by Inactivated Influenza Virus Vaccine", *J. Inf. Dis.*, 167:584–592 (Mar. 1993).

Rajakumar, A., et al, "Sequence of an influenza virus hemagglutinin determined directly from a clinical sample", *Proc. Natl. Acad. Sci. USA*, 87:4154–4158 (1990).

Rosen, L., "Hemagglutination with Animal Viruses", in *Fundamental Techniques in Virology*, K. Habel and N.P. Salzman, eds., Academic Press, New York, pp. 276–287 (1969).

Smith, G.E., et al., "Production of Human Beta Interferon in Insect Cells Infected with a Baculovirus Expression Vector", *Mol. and Cell. Biol.*, 3:2156–2165 (1983).

Update: Influenza Activity—United States and Worldwide, and Composition of the 1992–1993 Influenza Vaccine, *Morbidity and Mortality Weekly Report.*, U.S. Department of Health and Human Services, Public Health Service, 41:315–323 (1992).

(List continued on next page.)

*Primary Examiner*—Anthony C. Caputa

*Attorney, Agent, or Firm*—Curtis, Morris & Safford PC; Thomas J. Kowalski

[57] ABSTRACT

A method of preparing a recombinant influenza vaccine using DNA technology is provided. The resulting vaccine is a trivalent influenza vaccine based on a mixture of recombinant hemagglutinin antigens cloned from influenza viruses having epidemic potential. The recombinant hemagglutinin antigens are full length, uncleaved (HA0), glycoproteins produced from baculovirus expression vectors in cultured insect cells and purified under non-denaturing conditions. The process for cloning influenza hemagglutinin genes from influenza A and B viruses uses specially designed oligonucleotide probes and PCR. The cloned HA genes are then modified by deletion of the natural hydrophobic signal peptide sequences and replacing them with a new baculovirus signal peptide. A general approach for the efficient extraction and purification of recombinant HA protein produced in insect cells is also disclosed which can be adapted for the purification of rHA proteins from A sub-types and B type influenza viruses. The procedure produces substantially pure rHA which is a biologically active hemagglutinin, non-denatured, and suitable as a component in human or other animal influenza vaccines.

11 Claims, 3 Drawing Sheets

OTHER PUBLICATIONS

Update: Influenza Activity—United States, 1992–93 Season, *Morbidity and Mortality Weekly Report*, U.S. Department of Health and Human Services, Public Health Service, 42:51–53 (Jan. 1993).

Update: Influenza Activity—United States, 1992–93 Season, *Morbidity and Mortality Weekly Report*, U.S. Department of Health and Human Services, Public Health Service, 42:131, 137–138 (Feb. 1993).

Wang, M., et al, "Extensive Heterogeneity in the Hemagglutinin of Egg-Grown Influenza Viruses from Different Patients", *Virol*; ., 171:275–279 (1989).

Weiss, W., et al, "Structure of the influenza virus hemagglutinin complexed with its receptor, sialic acid" *Nature*, 333:426–431 (1988).

Wilson, I.A., "Structure of the haemagglutinin membrane glycoprotein of influenza virus at 3 A resolutoin", *Nature*, 289:366–378 (1981).

Stanley et al. Virology 56:640–45 1973.

Possee, R.D. Virus Research 5C17:43–59 1986.

Kuroda et al. The EMBO Journal 5(6):1359–1365 1986.

Matsuura et al. J. Gen. Virol. 68:1233–1250 1987.

Luckow et al. Bio/Technology 6:47–55 1988.

```
INFLUENZA VIRUS
STOCK FROM FDA
```
↓
VIRUS TITER (HEMAGGLUTINATION ASSAY)

INJECT 10 DAY OLD EGGS → ↓ ← OPTIMIZE 1. TPCK TRYPSIN
                                      2. FBS

↓                                    INFECT MDCK CELLS
FREEZE STOCK OF                      ↓
ALLANTOIC FLUID                      HARVEST VIRUS
↓                                    ↓
```
1. HEMAGGLUTINATION ASSAY
2. HA-INHIBITION ASSAY
3. VIRUS NEUTRALIZATION ASSAY
```
ISOLATE RNA:
  A STRAINS-VIRAL RNA
  B STRAINS-mRNA
↓
SYNTHESIZE cDNA:
  A STRAINS-UNIVERSAL
    PRIMER/VIRAL RNA
  B STRAINS-RANDOM
    PRIMERS/mRNA
↓
PCR TO AMPLIFY TOTAL
  HA GENE
↓
CLONE INTO E. coli PLASMID
↓
SEQUENCE 5' END TO IDENTIFY
SIGNAL PEPTIDE SEQUENCE
↓
PCR TO AMPLIFY HA GENE MINUS
  SIGNAL
↓
CLONE INTO BACULOVIRUS
  RECOMBINATION VECTOR
↓
TRANSFECT INSECT CELLS;
SELECT BACULOVIRUS
  EXPRESSION VECTOR
↓
PRODUCE rHA IN INSECT
  CELLS;
PURIFY HA ANTIGEN
↓
```
ANIMAL AND HUMAN VACCINE STUDIES
```

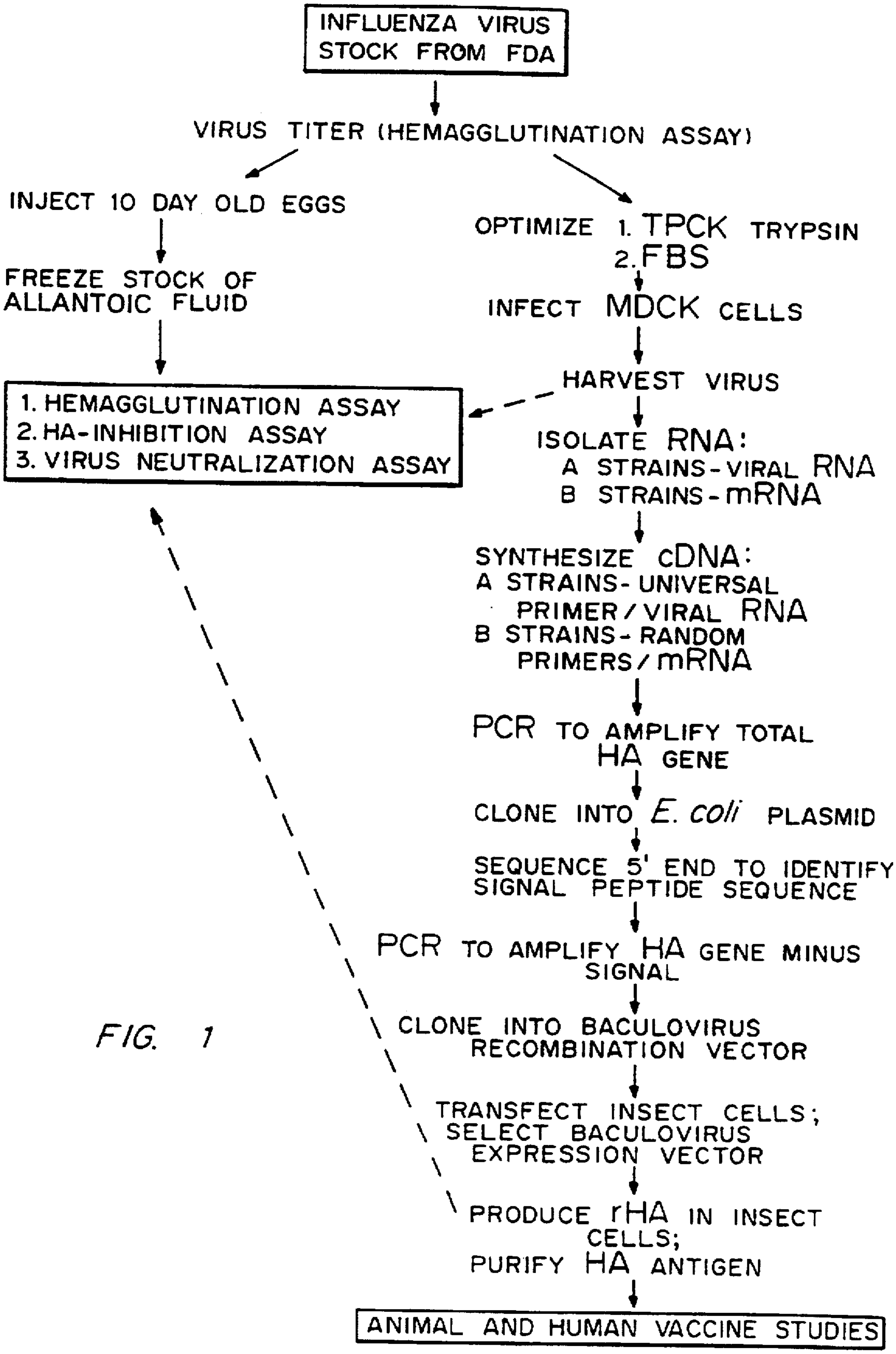

FIG. 1

METHOD FOR PRODUCING INFLUENZA HEMAGGLUTININ MULTIVALENT VACCINES USING BACULOVIRUS

BACKGROUND OF THE INVENTION

The present invention is generally in the area of recombinant influenza vaccines.

Epidemic influenza occurs annually and is a cause of significant morbidity and mortality worldwide. Children have the highest attack rate, and are largely responsible for transmission of influenza viruses in the community. The elderly and persons with underlying health problems are at increased risk for complications and hospitalization from influenza infection. In the United States alone, more than 10,000 deaths occurred during each of seven influenza seasons between 1956 and 1988 due to pneumonia and influenza, and greater than 40,000 deaths were reported for each of two seasons (Update: Influenza Activity—United States and Worldwide, and Composition of the 1992–1993 Influenza Vaccine, *Morbidity and Mortality Weekly Report.* U.S. Department of Health and Human Services, Public Health Service, 41/No. 18:315–323, 1992.)

Influenza viruses are highly pleomorphic particles composed of two surface glycoproteins, hemagglutinin (HA) and neuraminidase (NA). The HA mediates attachment of the virus to the host cell and viral-cell membrane fusion during penetration of the virus into the cell. The influenza virus genome consists of eight single-stranded negative-sense RNA segments of which the fourth largest segment encodes the HA gene. The influenza viruses are divided into types A, B and C based on antigenic differences. Influenza A viruses are described by a nomenclature which includes the sub-type or type, geographic origin, strain number, and year of isolation, for example, A/Beijing/353/89. There are at least 13 sub-types of HA (H1–H13) and 9 subtypes of NA (N1–N9). All subtypes are found in birds, but only H1–H3 and N1–N2 are found in humans, swine and horses (Murphy and Webster, "Orthomyxoviruses", in *Virology*, ed. Fields, B. N., Knipe, D. M., Chanock, R. M., 1091–1152 (Raven Press, New York, (1990)).

Antibodies to HA neutralize the virus and form the basis for natural immunity to infection by influenza (Clements, "Influenza Vaccines", in *Vaccines: New Approaches to Immunological Problems*, ed. Ronald W. Ellis, pp. 129–150 (Butterworth-Heinemann, Stoneham, Mass. 1992)). Antigenic variation in the HA molecule is responsible for frequent outbreaks to influenza and for limited control of infection by immunization.

The three-dimensional structure of HA and the interaction with its cellular receptor, sialic acid, has been extensively studied (Wilson, et al, "Structure of the hemagglutinin membrane glycoprotein of influenza virus at 3A° resolution" *Nature* 289:366–378 (1981); Weis, et al, "Structure of the influenza virus hemagglutinin complexed with its receptor, sialic acid" *Nature*, 333:426–431 (1988); Murphy and Webster, 1990). The HA molecule is present in the virion as a trimer. Each monomer exists as two chains, HA1 and HA2, linked by a single disulfide bond. Infected host cells produce a precursor glycosylated polypeptide (HA0) with a molecular weight of about 85,000, which is subsequently cleaved into HA1 and HA2.

The presence of influenza HA-specific neutralizing IgG and IgA antibody is associated with resistance to infection and illness (Clements, 1992). Inactivated whole virus or partially purified (split subunit) influenza vaccines are standardized to the quantity of HA from each strain. Influenza vaccines usually include 7 to 25 micrograms HA from each of three strains of influenza.

The role of the other major surface glycoprotein, NA, in protective immunity of antibody or T-cell responses against influenza has not been defined. Neuraminidase is very labile to the process of purification and storage (Murphy and Webster, 1990) and the quantity of NA in the current influenza vaccines is not standardized. Purified HA but not NA vaccine prevents disease in animals challenged with influenza (Johansson, et al, "Purified influenza virus hemagglutinin and neuraminidase are equivalent in stimulation of antibody response but induce contrasting types of immunity to infection" *J. Virology*, 63:1239–1246 (1989)). An experimental vaccine based on neuraminidase antigen was not found to be protective in a human trial (Orga et al, *J. Infect. Dis.* 135:499–506 (1977)).

Licensed influenza vaccines consist of formalin-inactivated whole or chemically split subunit preparations from two influenza A subtype (H1N1 and H3N2) and one influenza B subtype viruses. Prior to each influenza season, the U.S. Food and Drug Administration's Vaccines and Related Biologicals Advisory Committee recommends the composition of a trivalent influenza vaccine for the upcoming season. The 1992–93 vaccine contained A/Texas/36/91-like(H1N1), A/Beijing/353/89-like(H3N2), and B/Panama/45/90 viruses. The FDA has advised that the 1993–94 influenza vaccine should contain the same Texas and Panama strains and a new influenza A Beijing strain (A/Beijing/32/92).

Vaccination of high-risk persons each year before the influenza season is the most effective measure for reducing the impact of influenza. Limitations of the currently available vaccines include low use rates; poor efficacy in the elderly and in young children; production in eggs; antigenic variation; and adverse reactions.

The Center for Disease Control (CDC) estimates that less than 30% of the individuals at high-risk for influenza are vaccinated each year (MMWR, 1992). The current inactivated vaccines achieve a high rate of protection against disease among normal healthy adults when the antigens of the vaccine and those of the circulating influenza viruses are closely related. Among the elderly, the rate of protection against illness is much lower, especially for those who are institutionalized (Clements, 1992). In a recent study by Powers and Belshe, *J. Inf. Dis.* 167:584–592 (1993), significant antibody responses to a trivalent subvirion influenza vaccine were observed in less than 30 percent of subjects 65 years old or older.

Seed viruses for influenza A and B vaccines are naturally occurring strains that replicate to high titers in the allantoic cavity of chicken eggs. Alternatively, the strain for the influenza A component is a reassortant virus with the correct surface antigen genes. A reassortant virus is one that, due to segmentation of the viral genome, has characteristics of each parental strain. When more than one influenza viral strains infect a cell, these viral segments mix to create progeny virion containing various assortments of genes from both parents.

Protection with current whole or split influenza vaccines is short-lived and wanes as antigenic drift occurs in epidemic strains of influenza. Influenza viruses undergo antigenic drift as a result of immune selection of viruses with amino acid sequence changes in the hemagglutinin molecule. Ideally, the vaccine strains match the influenza virus strains causing disease. The current manufacturing process for influenza vaccines, however, is limited by propagation of the virus in embryonated chicken eggs. Not all influenza virus strains replicate well in eggs; thus the viruses must be adapted or viral reassortants constructed. Extensive heterogeneity occurs in the hemagglutinin of egg-grown influenza viruses as compared to primary isolates from infected individuals grown in mammalian cells (Wang, et al, *Virol.* 171:275–279 (1989); Rajakumar, et al. *Proc. Natl. Acad. Sci. USA* 87:4154–4158 (1990)). The changes in HA during the selection and manufacture of influenza vaccines can result in a mixture of antigenically distinct subpopulations of virus. The viruses in the vaccine may therefore differ from the variants within the epidemic strains, resulting in suboptimal levels of protection.

Immediate hypersensitivity reactions can occur in persons with severe egg allergy due to residual egg protein in the vaccine. The 1976 swine influenza vaccine was associated with an increased frequency of Guillain-Barré syndrome. Subsequent vaccines prepared from other influenza strains have, thus far, not been observed to increase the occurrence of this rare disease.

A method of producing an influenza vaccine that does not require propagation in eggs would result in a purer product that would be less likely to cause an adverse immune reaction. In addition, a purer vaccine preparation would not require virus inactivation or organic extraction of viral membrane components, thereby avoiding denaturation of antigenic epitopes and safety concerns due to residual chemicals in the vaccine.

In addition, an influenza vaccine produced in the absence of egg propagation would avoid the genetic heterogeneity that occurs during adaptation and passage through eggs. This would result in a vaccine that is better matched with influenza epidemic strains, resulting in improved efficacy.

It is therefore an object of the present invention to provide a method of producing an influenza vaccine that does not require replication in eggs.

It is a further object of the present invention to provide a method of producing an influenza vaccine that is rapid and cost-efficient, highly purified and allows production of vaccines from primary sources of influenza.

SUMMARY OF THE INVENTION

A method of preparing a recombinant influenza hemagglutinin protein by expression in insect cells using a baculovirus expression system is provided. The resulting protein is useful in making vaccine consisting of a trivalent influenza vaccine based on a mixture of recombinant hemagglutinin antigens cloned from influenza viruses having epidemic potential. The recombinant hemagglutinin proteins are full length, uncleaved (HA0) glycoproteins purified under non-denaturing conditions to 95% or greater purity. The recombinant HA0 glycoproteins can be cleaved at the disulfide bond to form the two chains, HA1 and HA2.

A process for cloning influenza hemagglutinin genes from influenza A and B viruses using specially designed oligonucleotide probes and polymerase chain reaction (PCR) methodology is also disclosed. The cloned HA genes are modified by deletion of the natural hydrophobic signal peptide sequences and replacement with a new baculovirus signal peptide. These chimeric genes are introduced into baculovirus expression vectors so that the baculovirus polyhedrin promoter directs the expression of recombinant HA proteins in infected insect cells. The 18 amino acid baculovirus signal peptide directs the translation of rHA into the insect cell glycosylation pathway and is not present on the mature rHA glycoprotein.

This methodology can be extended to all types of influenza viruses, including but not limited to the prevalent A (H1N1) sub-type, the A(H3N2) sub-type, and the B type that infect humans, as well as the influenza viruses which infect other mammalian and avian species.

A general approach for the efficient extraction and purification of recombinant HA protein produced in insect cells is disclosed which can be adapted for the purification of rHA proteins from A sub-types and B type influenza viruses. The recombinant vaccine can be developed from primary sources of influenza, for example, nasal secretions from infected individuals, rather than from virus adapted to and cultured in chicken eggs. This allows rapid development of vaccine directly from epidemic strains of influenza and avoids the problems arising from adaptation of the virus for culture in eggs, as well as patient reaction to egg contamination in the resulting vaccine. In one embodiment, the vaccine is formulated in an immunizing dosage form including purified rHA antigens from three strains of influenza virus recommended by the FDA for the 1993/94 influenza epidemic season. Functional immunity can be measured using assays that quantitate antibodies that bind to influenza hemagglutinin, that block the ability of influenza virus to agglutinate red blood cells, or that neutralize the influenza virus. Protective immune responses with rHA vaccines can also be measured in animals that are susceptible to influenza infection or in human challenge studies.

BRIEF DESCRIPTION OF THE DRAWINGS

FIG. 1 is a schematic of the cloning of HA genes from influenza A strains from purified viral RNA preparations, purification of expressed rHA, and biological characterization of rHA. Abbreviations: FDA, Food and Drug Administration; MDCK, Madin Darby Canine Kidney; TPCK, tosylphenylalanylchloromethylketone; RNA, ribonucleic acid; cDNA, complementary deoxyribonucleic acid; HA, hemagglutinin; FBS, Fetal Bovine Serum; PCR, Polymerase Chain Reaction; and BV, Baculovirus.

DETAILED DESCRIPTION OF THE INVENTION

Figure 2:
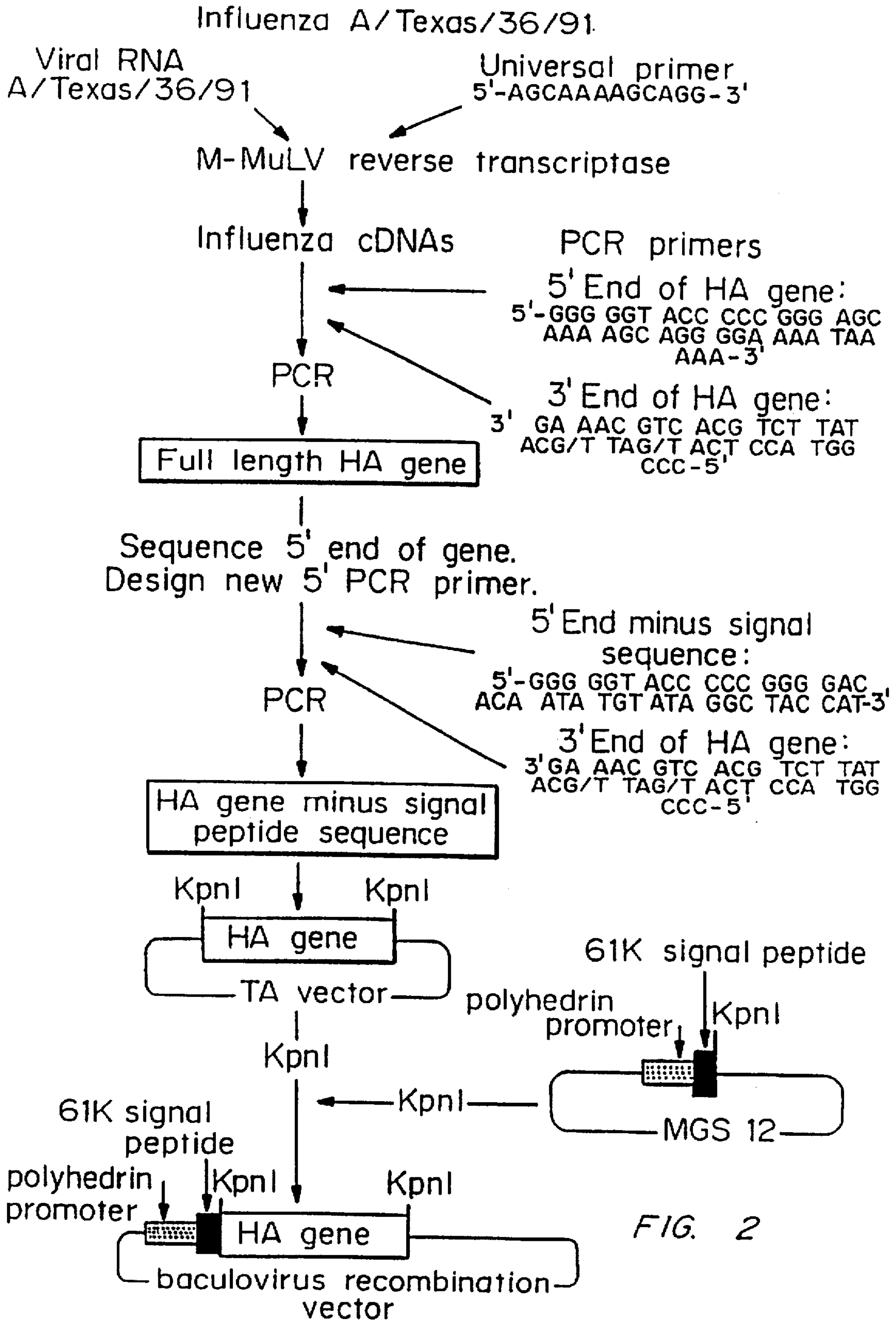
FIG. 2 is a more detailed schematic of the method of FIG. 1 applied to the cloning and expression of the HA gene of the Influenza A/Texas/36/91 strain. Influenza HA gene was obtained from RNA purified from MDCK cells infected with influenza A/Texas/36/91 using reverse transcriptase and a universal primer (SEQ ID NO.1) followed by two rounds of PCR amplification and cloning, wherein the 5' and 3' primers shown in the first round are set forth in SEQ ID NOs. 2 and 3, respectively, and wherein the 5' and 3' primers shown in the second round are set forth in SEQ ID NOs. 4 and 3, respectively. A baculovirus recombination vector was constructed containing the polyhedrin promoter and a signal peptide sequence from the baculovirus 61K gene (a baculovirus gene that encodes a signal peptide having a molecular weight of approximately 61,000), followed by the complete coding sequences for the mature HA protein. This recombination vector was then used to make a baculovirus expression vector that produces HA from this strain of the virus.

A method of preparing a recombinant influenza vaccine is described. A full length, uncleaved (HA0), hemagglutinin antigen from an influenza virus is produced with baculovirus expression vectors in cultured insect cells and purified under non-denaturing conditions. Two or more purified hemagglutinin antigens from influenza A and/or influenza B strains are mixed together to produce a multivalent influenza vaccine. The recombinant antigens may be combined with an adjuvant carrier for increased efficacy.

The use of recombinant DNA technology to produce influenza vaccines offers several advantages: a recombinant DNA influenza vaccine can be produced under safer and more stringently controlled conditions; propagation with infectious influenza in eggs is not required; recombinant HA protein can be more highly purified, virtually eliminating side effects due to contaminating proteins; purification procedures for recombinant HA do not have to include virus inactivation or organic extraction of viral membrane components, therefore avoiding denaturation of antigens and additional safety concerns due to residual chemicals in the vaccine; production of HA via recombinant DNA technology provides an opportunity to avoid the genetic heterogeneity which occurs during adaptation and passage through eggs, which should make it possible to better match vaccine stains with influenza epidemic stains, resulting in improved efficacy; and a recombinant approach may also allow for strain selection later in the year, thereby allowing time for selections based on more reliable epidemiological data.

Baculovirus Expression System

Baculoviruses are DNA viruses in the family Baculoviridae. These viruses are known to have a narrow host-range that is limited primarily to Lepidopteran species of insects (butterflies and moths). The baculovirus *Autographa californica* Nuclear Polyhedrosis Virus (AcNPV), which has become the prototype baculovirus, replicates efficiently in susceptible cultured insect cells. AcNPV has a double-stranded closed circular DNA genome of about 130,000 base-pairs and is well characterized with regard to host range, molecular biology, and genetics.

Many baculoviruses, including AcNPV, form large protein crystalline occlusions within the nucleus of infected cells. A single polypeptide, referred to as a polyhedrin, accounts for approximately 95% of the protein mass of these occlusion bodies. The gene for polyhedrin is present as a single copy in the AcNPV viral genome. Because the polyhedrin gene is not essential for virus replication in cultured cells, it can be readily modified to express foreign genes. The foreign gene sequence is inserted into the AcNPV gene just 3' to the polyhedrin promoter sequence such that it is under the transcriptional control of the polyhedrin promoter.

Recombinant baculoviruses that express foreign genes are constructed by way of homologous recombination between baculovirus DNA and chimeric plasmids containing the gene sequence of interest. Recombinant viruses can be detected by virtue of their distinct plaque morphology and plaque-purified to homogeneity.

Baculoviruses are particularly well-suited for use as eukaryotic cloning and expression vectors. They are generally safe by virtue of their narrow host range which is restricted to arthropods. The U.S. Environmental Protection Agency (EPA) has approved the use of three baculovirus species for the control of insect pests. AcNPV has been applied to crops for many years under EPA Experimental Use Permits.

AcNPV wild type and recombinant viruses replicate in a variety of insect cells, including continuous cell lines derived from the fall armyworm, *Spodoptera frugiperda* (Lepidoptera; Noctuidae). *S. frugiperda* cells have a population doubling time of 18 to 24 hours and can be propagated in monolayer or in free suspension cultures.

Recombinant HA proteins can be produced in, but not limited to, cells derived from the Lepidopteran species *Spodoptera frugiperda*. Other insect cells that can be infected by baculovirus, such as those from the species *Bombix mori, Galleria mellanoma, Trichplusia ni,* or *Lamanthria dispar,* could also be used as a suitable substrate to produce recombinant HA proteins.

The most preferred host cell line for protein production from recombinant baculoviruses is Sf900+. Another preferred host cell line for protein production from recombinant baculoviruses is Sf9. Sf900+ and Sf9 are non-transformed, non-tumorigenic continuous cell lines derived from the fall armyworm, *Spodoptera frugiperda* (Lepidoptera; Noctuidae). Sf900+ and Sf9 cells are propagated at 28°±2° C. without carbon dioxide supplementation. The culture medium used for Sf9 cells is TNMFH, a simple mixture of salts, vitamins, sugars and amino acids, supplemented with 10% fetal bovine serum. Aside from fetal bovine serum, no other animal derived products (i.e. trypsin, etc.) are used in cell propagation. Serum free culture medium (available as Sf900 culture media, Gibco BRL, Gaithersburg, Md.) can also be used to grow Sf9 cells and is preferred for propagation of Sf900+ cells.

Sf9 cells have a population doubling time of 18–24 hours and can be propagated in monolayer or in free suspension cultures. *S. frugiperda* cells have not been reported to support the replication of any known mammalian viruses.

It will be understood by those skilled in the art that the expression vector is not limited to a baculovirus expression system. The recombinant HA proteins can also be expressed in other expression vectors such as Entomopox viruses (the poxviruses of insects), cytoplasmic polyhedrosis viruses (CPV), and transformation of insect cells with the recombinant HA gene or genes constitutive expression.

Isolation of Influenza Strains

One or more influenza strains are isolated from individuals infected with the disease. Preferably, the influenza strains are those identified by the Food and Drug Administration (FDA) or CDC to have epidemic potential for the subsequent influenza season. An advantage of the method described herein is that clinical samples, such as nasal secretions, from patients infected with influenza can be used as a direct source of virus. Alternatively, they can be obtained from the FDA or CDC.

Propagation of Influenza Strains

The strains are then propagated in cells producing high viral titers, such as Madin Darby Canine Kidney (MDCK) cells (available from the American Type Culture Collection under accession number ATCC CCL34). For example, MDCK cells are infected in the presence of tosylphenylalanyl chloromethylketone (TPCK) partially inactivated trypsin and fetal bovine serum concentrations optimized to produce the highest titers of first passage virus. The MDCK cells are infected with the influenza strains at a low multiplicity of infection (0.1 to 0.5) as determined by a standard HA assay (Rosen, "Hemagglutination with Animal Viruses" in *Fundamental Techniques in Virology,* ed. K. Habel and N. P. Salzman, pp. 276–28 (Academic Press, New York 1969), the teachings of which are incorporated herein). The infected cells are incubated at 33° C. for 48 hours, and the media assayed for virus production using the hemagglutination activity assay. The conditions yielding the highest HA activity are then used to prepare large stocks of influenza virus.

Purification of Virus

Viral particles produced from the first passage are purified from the media using a known purification method such as sucrose density gradient centrifugation. For example, virus is harvested 24–48 hours post infection by centrifuging media of influenza infected MDCK cells. The resulting viral pellet is resuspended in buffer and centrifuged through a buffered sucrose gradient. The influenza virus band is harvested from the 40–45% sucrose region of the gradient, diluted with buffer and pelleted by centrifugation at 100,000 x g. The purified virus pellet is resuspended in buffer and stored at −70° C.

Cloning of Influenza Hemagglutinin Genes

An overview of the methods for cloning HA genes is provided in FIG. 1. Basically, cells are infected with the influenza strain to be cloned. Virus is harvested from the cell media and either viral RNA, for Influenza A strains, or mRNA, for Influenza B strains, is isolated. Viral RNA (-RNA) is extracted from purified virions and analyzed on formaldehyde agarose gels using standard procedures. cDNA is synthesized, using either an universal primer system for the viral RNA from the Influenza A strains or random primers for the mRNA from Influenza B strains. Plus-standard complimentary DNA (cDNA) is made using a universal oligonucleotide primer (5'-AGCAAAAGCAGG-3' (SEQ ID NO. 1)) which is homologous to all hemagglutinin RNA segments in influenza A and B viruses (Davis et al, "Construction and characterization of a bacterial clone containing the hemagglutinin gene of the WSN strain (H0N1) of influenza virus" *Gene,* 10:205–218 (1980)). Primers are designed that are homologous to conserved regions at the 5' and 3' end of influenza hemagglutinin genes. Both 5' and 3' primers also have restriction enzyme sites at the ends that are not found within the hemagglutinin genes.

The appropriate influenza A or B primers and influenza cDNA are mixed and the hemagglutinin gene segments amplified using standard PCR procedures. The resulting double-stranded DNA fragments contain entire mature hemagglutinin coding sequences. The polymerase chain reaction ("PCR") is used to amplify the total HA gene, which is then cloned into a suitable bacterial host such as *E. coli*. The 5' ends are sequenced to identify the signal peptide of the HA genes, then PCR is used to amplify the HA genes minus the signal peptide. This is then subcloned into a plasmid transfer vector containing the AcNPV polyhedrin promoter. The resulting transfer vectors contain the following 5'→3' sequences: Polyhedrin promoter from the baculovirus *A. californica* NPV, an ATG translational start codon, a 61K baculovirus signal peptide, the coding sequences for mature hemagglutinin, the natural hemagglutinin translational termination codon, the polyhedrin RNA polyadenalytion signal, and flanking baculovirus DNA.

A purified chimeric transfer plasmid DNA containing a cloned hemagglutinin gene is then mixed with AcNPV wild type DNA, co-precipitated with calcium and transfected into *S. frugiperda* cells. Recombinant baculoviruses are selected on the basis of plaque morphology and further purified by additional rounds of plaque-purification. Cloned recombinant baculoviruses are screened for hemagglutinin expression and a single baculovirus expression vector is selected to produce a Master Virus Bank.

Influenza A Strains:

HA genes from influenza A strains are cloned from purified viral RNA preparations. Viral RNA is extracted from 100–200 microliters of purified influenza A virions containing 1,000–2,000 hemagglutination units (HAU) of influenza. One HAU is the amount of virus that will agglutinate 50% of the red blood cells in the standard agglutination assay (Rosen, 1969). The virions are treated with proteinase K to digest protein, then the viral RNA is extracted with equal volumes of phenol and chloroform, and precipitated with ethanol in the presence of tRNA carrier. The viral RNA is resuspended in buffer and digested with RNAse-free DNAse to remove any contaminating DNA, then the extraction and precipitation steps repeated. Viral RNA (vRNA) is then analyzed using formaldehyde agarose gels as described by Maniatis, et al. Molecular Cloning: A Laboratory Manual, pp. 86–96 and 366–367 (Cold Spring Harbor Lab., Cold Spring, N.Y. 1982).

Influenza B Strains:

HA genes from influenza B strains are cloned from total messenger RNA (mRNA) extracted from cells infected with the influenza B-strain. Total RNA is then extracted from the infected cells. The harvested cells are lysed in the presence of guanidinium thiocyanate and total cell RNA is purified, using, for example, the RNA Extraction Kit from Pharmacia Biotech Inc. (Piscataway, N.J.) Total mRNA is extracted from cellular RNA using Oligo-(dT)-cellulose spun columns, using, for example, the mRNA Purification Kit from Pharmacia Biotech Inc.

Expression and Processing of Recombinant hemagglutinin in Insect Cells

Recombinant hemagglutinin antigens are expressed at high levels in *S. frugiperda* cells infected with AcNPV-hemagglutinin vectors. The primary gene product is unprocessed, full length hemagglutinin (rHA0) and is not secreted but remains associated with peripheral membranes of infected cells. This recombinant HA0 is a 68,000 molecular weight protein which is glycosylated with N-linked, high-mannose type glycans. There is evidence that rHA0 forms trimers post-translationally which accumulate in cytoplasmic membranes.

Purification of Recombinant HA0

Several days post infection, rHA0 can be selectively extracted from the peripheral membranes of AcNPV-hemagglutinin infected cells with a non-denaturing, nonionic detergent or other methods known to those skilled in the art for purification of recombinant proteins from insect cells, including, but not limited to affinity or gel chromatography, and antibody binding. The detergent soluble rHA0 is further purified using DEAE ion exchange and lentil lectin affinity chromatography, or other equivalent methods known to those skilled in the art.

Purified rHA0 is resuspended in an isotonic, buffered solution. Following the removal of the detergent, purified rHA0 will efficiently agglutinate red blood cells.

Structural and Biological Properties of Recombinant HA0 rHA0 is purified to at least 95% purity. This migrates predominantly as a single major polypeptide of 68,000 molecular weight on an SDS-polyacrylamide gel. The quaternary structure of purified recombinant HA0 antigen was examined by electron microscopy, trypsin resistance, density sedimentation analysis, and ability to agglutinate red blood cells. These data show that recombinant HA0 forms trimers, which assemble into rosettes.

Purified rHA0 does not agglutinate cells prior to removal of detergent, suggesting that the antigen must form complexes (rosettes) in order to cross-link chicken red blood cells. The quantitative ability of purified rHA0 to agglutinate cells is used as a measure of lot-to-lot consistency of the antigen. One hemagglutinin unit is defined as the quantity of antigen required to achieve 50% agglutination in a standard hemagglutinin assay with chicken red blood cells. Comparative data shows that purified rHA0 antigens agglutinate red blood cells with an efficiency comparable to that observed with whole influenza virions.

The recombinant HA0 can be cleaved at the disulfide bond, causing a conformation change that results in the formation of two chains, HA1 and HA2 as described by Carr, C. M. and Kim, P. S., "A Spring-loaded Mechanism for the Conformational Change of Influenza Hemagglutin", *Cell* 73:823–832 (1993), which is incorporated by reference herein. Cleavage of recombinant HA0 is described in more detail below in Example 6. It is believed that, upon cleavage of HA0 into HA1 and HA2, the chains become infectious by acquiring the ability to fuse with a cell, thereby creating an improved immune response. The processing of antigens such as influenza hemagglutin occurs by the binding of antigenic peptides to major histocompatibility (MHC) molecules. The antigen/MHC complex is recognized by T cells to initiate an immune response as described in the review by Harding and Geuze, *Current Opinion in Cell Biology* 5:596–605 (1993), which is incorporated by reference herein.

Formulation and Packaging of Vaccines

The rHA can be formulated and packaged, alone or in combination with other influenza antigens, using methods and materials known to those skilled in the art for influenza vaccines. In a preferred embodiment, HA proteins from two A strains and one B strain are combined to form a multivalent vaccine.

In a particularly preferred embodiment, the HAs are combined with an adjuvant, in an amount effective to enhance the immunogenic response against the HA proteins. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, new chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapasulation of the protein in lipid vesicles such as NOVASOME™ lipid vesicles (Micro Vescular Systems, Inc., Nashua, N.H.) should also be useful.

In the preferred embodiment, the vaccine is packaged in a single dosage for immunization by parenteral (i.e., intramuscular, intradermal or subcutaneous) administration or nasopharyngeal (i.e., intranasal) administration. The effective dosage is determined as described in the following examples. The carrier is usually water or a buffered saline, with or without a preservative. The antigen may be lyophilized for resuspension at the time of administration or in solution.

The carrier may also be a polymeric delayed release system. Synthetic polymers are particularly useful in the formulation of a vaccine to effect the controlled release of antigens. An early example of this was the polymerization of methyl methacrylate into spheres having diameters less than one micron to form so-called nano particles, reported by Kreuter, J., *Microcapsules and Nanoparticles in Medicine and Pharmacology*, M. Donbrow (Ed). CRC Press, p. 125–148. The antibody response as well as the protection against infection with influenza virus was significantly better than when antigen was administered in combination with alumium hydroxide. Experiments with other particles have demonstrated that the adjuvant effect of these polymers depends on particle size and hydrophobicity.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,l-lactide-co-glycolide) (PLGA). This is a biodegradable polyester that has a long history of medical use in erodible sutures, bone plates and other temporary prostheses, where it has not exhibited any toxicity. A wide variety of pharmaceuticals including peptides and antigens have been formulated into PLGA microcapsules. A body of data has accumulated on the adaptation of PLGA for the controlled release of antigen, for example, as reviewed by Eldridge, J. H., et al. *Current Topics in Microbiology and Immunology*. 1989, 146: 59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

The present invention will be further understood by reference to the following non-limiting examples.

EXAMPLE 1

Propagation and Purification of Influenza Viruses

The following influenza vaccine strains were obtained from the FDA in chicken egg allantoic fluid:

| |
|---|
| A/Beijing/353/89-like (H3N2) |
| A/Beijing/32/92-like (H3N2) |
| A/Texas/36/91-like (H1N1) |
| B/Panama/45/90 |

To propagate the original stock of influenza virus obtained from the FDA, MDCK cells were infected in the presence of TPCK-treated trypsin (Sigma Chemical Co., St. Louis, Mo.) and fetal bovine serum concentrations optimized to produce the highest titers of first passage virus. The MDCK cells were infected with the influenza strains at a low multiplicity of infection (0.1 to 0.5) as determined by a standard HA assay (Rosen, "Hemagglutination with Animal Viruses" in *Fundamental Techniques in Virology*, ed. K. Habel and N. P. Salzman, pp. 276–28 (Academic Press, New York 1969)). The infected cells were incubated at 33° C. for 48 h. and media was assayed for virus production using the hemagglutination activity assay. The conditions yielding the highest HA activity were used to prepare large stocks of influenza virus. The optimum concentrations of TPCK trypsin and fetal bovine serum for the above influenza viruses are listed in Table 1.

TABLE 1

Optimum Concentration of TPCK Trypsin and Fetal Bovine Serum.

| | A/Beijing/ 353/89 | A/Beijing/ 32/92 | A/Texas/ 36/91 | B/Panama/ 45/90 |
|---|---|---|---|---|
| % Fetal Bovine Serum | 0.25% | 0.25% | 0.25% | 5.0% |
| Amount TPCK Treated Trypsin | 45 μ/ml | 45 μg/ml | 45 μ/ml | 3 μ/ml |

Purification of Influenza Virus:

Virus was harvested 24–48 hours post infection from 10 T175 tissue culture flasks by clarifying media (1,000 x g for 10 minutes) of influenza infected MDCK cells. The virus was pelleted from the media at 100,000 x g for 1 hour. The resulting viral pellet was resuspended in 1 ml phosphate buffered saline (PBS) pH 7.4 and centrifuged through a 20 ml 20–60% (w/v) sucrose gradient in PBS. The influenza virus band was harvested from the 40–45% sucrose region of the gradient, diluted with PBS and pelleted at 100,000 x g. The purified virus pellet was resuspended in 0.5 ml PBS stored at −70° C.

EXAMPLE 2

Cloning of Influenza A/Texas/36/91 HA Gene

A specific example of the cloning step for one of the influenza HA genes is shown in FIG. 2. Viral RNA was extracted as described above from Influenza A/Texas/36/91, obtained from the CDC. The universal primer complementary to the 3' end of influenza RNA segments 5'-AGCAAAAGCAGG-3' (SEQ ID NO. 1) was used with murine Maloney Leukemia Virus (M-MuLV) reverse transcriptase to produced influenza cDNAs. Purified viral RNA or mRNA (5 μg) was used as a template to make cDNA utilizing M-MuLV reverse transcriptase supplied in the First-Strand cDNA Synthesis Kit by Pharmacia Inc. The primer used for cDNA of viral RNA from influenza A strains was a synthetic oligonucleotide primer (5'-AGCAAAAGCAGG-3') (SEQ ID NO. 1), which is homologous to the 3' end of all HA gene virion segments.

Amplification of HA genes from cDNA was done by polymerase chain reaction (PCR) using standard reaction conditions (Gene Amp kits; Cetus/Perkin Elmer, Norwalk, Conn.). The PCR reaction mixture (100 μl) contained 20 pmol of primers specific for 5' and 3' ends of the HA gene of influenza A (H3) or A (H1) or influenza B strains as determined by consensus sequences found in GenBank DNA data files, as shown in Table 2. Amplification was carried out for 30 cycles with each cycle consisting of 1 minute of denaturation at 94° C., 2 minutes at 55° C. for reanealing and 3 minutes at 72° C. for extension. The PCR products were analyzed on 0.8% agarose gels for correct size before cloning.

PCR primers from the 5' end of the HA gene: 5'-GGG GGT ACC CCC GGG AGC AAA AGC AGG GGA AAA TAA AAA-3' (SEQ ID NO. 2) and 3' end of the HA gene: 3'-GA AAC GTC ACG TCT TAT ACG/T TAG/T ACT CCA TGG CCC-5' (SEQ ID NO. 3) were used in the PCR to yield the full length HA gene.

A new 5' PCR primer was designed from the 5' end of the gene: 5' end minus signal sequence: 5'-GGG GGT ACC CCC GGG GAC ACA ATA TGT ATA GGC TAC CAT-3' (SEQ ID NO. 4) and the 3' end of the gene: 3'-GA AAC GTC ACG TCT TAT ACG/T TAG/T ACT CCA TGG CCC-5' (SEQ ID NO. 3). These were used in PCR to yield the HA gene minus the signal peptide sequence. This was then inserted into the TA vector cleaved with KpnI. The 61K signal peptide for baculovirus expression and the polyhedrin promoter were then inserted into the TA vector containing the HA gene minus influenza signal peptide sequence. The resulting baculovirus recombination vector contains the polyhedrin promoter, 61K baculovirus signal peptide, and HA gene for Influenza A/Texas/36/91.

HA genes from influenza B strains were cloned from total messenger RNA (mRNA) extracted from MDCK cells infected with the influenza B-strain B/Panama/45/90. Total RNA was prepared from 5 T175 flasks of infected cells. The harvested cells were lysed in the presence of guanidinium thiocyanate and total cell RNA was purified as described above. Total mRNA was extracted from cellular RNA using Oligo-(dT)-cellulose spun columns as described above.

The primer used for mRNA from influenza B strains was a random oligonucleotide DNA primer (Pharmacia, Inc.).

TABLE 2

Primers Used for PCR Amplification.

| | |
|---|---|
| A/Beijing/32/93 | |
| 5' end gene SEQ ID NO 5 | 5' GGG GGA TCC GGT ACC AGC AAA AGC AGG GGA TAA TTC TAT 3'<br>BamH1 Kpn1 |
| 5' end minus HA signal peptide SEQ ID NO 12 | 5' GGG GGT ACC CCC GGG GAC TTT CCA GGA AAT GAC AAC AG 3'<br>Kpn1 Sma1 |
| 3' end SEQ ID NO 13 | 3' TAA TTA ATT TTT GTG GGA ACA AAG ATC CTA CTA AGC CAT GGC CC 5' |

TABLE 2-continued

| Primers Used for PCR Amplification. | |
|---|---|
| | Kpn1 |
| A/Texas/36/91 | |
| 5' end gene SEQ ID NO 2 | 5' GGG GGT ACC CCC GGG AGC AAA AGC AGG GGA AAA TAA AAA 3'<br>Kpn1 Sma1 |
| 5' end minus HA signal peptide SEQ ID NO 4 | 5' GGG GGT ACC CCC GGG GAC ACA ATA TGT ATA GGC TAC CAT 3'<br>Kpn1 Sma1 |
| 3' end SEQ ID NO: 3 | 3' GA AAC GTC ACG TCT TAT ACG/T TAG/T ACT CCA TGG CCC 5'<br>Kpn1 |
| B/Panama/45/90 | |
| 5' end gene SEQ ID NO: 14 | 5' GGG GAA TTC GGT ACC CCC GGG AAG GCA ATA ATT GTA CTA CTC ATG GT 3'<br>EcoR1 Kpn1 Sma1 |
| 5' end minus HA signal peptide SEQ ID NO: 15 | 5' GGT ACC CCC GGG GAT CGA ATC TGC ACT GGG ATA ACA 3'<br>Kpn1 Sma1 |
| 3' end SEQ ID NO: 16 | 3' TG TTA CAA AGA ACA/G AGG TAG ACA GAC ACT CCA TGG CCT AGG CTT AAG GGG 5'<br>Kpn1 BamH1 EcoRI |

An example of cDNA synthesis products used influenza virus A/Texas/36/91 viral RNA as a template. The location of the cDNA segments that code for the influenza proteins could be determined as follows. Purified viral RNA was combined in the reaction mixture with the universal single stranded DNA primer 5'-AGCAAAAGCAGG-3' (SEQ ID NO:1). This primer is complementary to the 3' end of influenza virion segments, as described above. The reaction also contained the addition of [$\alpha$-$^{32}$P]dCTP to visualize the cDNA products which were separated on 1.5% alkaline hydrolysis gel (Maniatis, et al, 1982) and exposed to X-OMAT-AR™ film.

EXAMPLE 3

Cloning HA Genes Into Bacterial Plasmids

The PCR amplified rHA genes were cloned into a pUC-like plasmid vector using the TA Cloning System (Invitrogen, Inc.). The presence of HA genes were verified by restriction enzyme digest analysis of plasmid DNA purified by standard procedures (Maniatis, et al, 1982). The 5' end of the rHA genes were then analyzed by DNA sequencing and new primers were designed to remove the sequences coding for the hydrophobic signal peptides at the N-terminus HA proteins. The specific 5' and 3' oligonucleotide primers listed in Table 2 were then used to amplify cDNA products by PCR and cloned into *E. coli* TA plasmid vectors (Invitrogen, Inc.) using standard cloning methods. The resulting DNA clones contained coding sequences for the mature HAs.

The rHA genes from A/Texas/36/91, A/Beijing/353/89, A/Beijing/32/92, and B/Panama/45/90 were subcloned by standard procedures (Maniatis et al, 1982) into baculovirus expression vectors. The HA genes were removed from the TA cloning plasmids with the appropriate restriction enzymes and the purified HA DNA fragment inserted into a baculovirus recombination plasmid. The resulting bacterial clones were screened for ampicillin resistance and then cut with restriction enzymes to release the inserted HA gene to confirm is presence. The recombination plasmids containing HA genes were purified on cesium chloride-ethidium bromide gradients (Maniatis, et al, 1982). The 5' end of the plasmids were sequenced to determine the presence of the correct baculovirus signals (AcNPV polyhedrin promoter, ATG translational start signal and baculovirus signal peptide sequence) and proper HA coding sequence in the correct reading frame. The DNA sequences at the 5' end of the HA genes and flanking AcNPV polyhedrin promoter and baculovirus signal peptide (first 18 amino acids of each amino acid sequence) are shown as SEQUENCE LISTINGS.

SEQ ID NO. 6 encodes the 5' end sequence of the HA gene for A/Beijing/32/92 (sequence range 1–481). SEQ ID NO. 7 is the corresponding amino acid sequence (beginning at the start codon "ATG" [nucleotide 21] of SEQ ID NO. 6). The amino acid sequence of the 61K signal peptide is set forth in SEQ ID NO. 7 as amino acids 1–18.

SEQ ID NO. 8 encodes the 5' end sequence of the HA gene for A/Texas/36/91 (sequence range 1–481). SEQ ID NO. 9 is the corresponding amino acid sequence (beginning at the start codon "ATG" [nucleotide 21] of SEQ ID NO. 8). The amino acid sequence of the 61K signal peptide is set forth in SEQ ID NO. 9 as amino acids 1–18.

SEQ ID NO. 10 encodes the 5' end sequence of the HA gene for B/Panama/45/90 (sequence range 1–434). SEQ ID NO. 11 is the corresponding amino acid sequence (beginning at the start codon "ATG" [nucleotide 21] of SEQ ID NO. 10). The amino acid sequence of the 61K signal peptide is set forth in SEQ ID NO. 11 as amino acids 1–18.

In SEQ ID NOs 6, 8, and 10, nucleotides 1–20 are the 3' end of the polyhedrin promoter, nucleotides 21–74 encode the 61K signal peptide, and nucleotides 75 to the end encode the 5' end of the HA gene.

EXAMPLE 4

Expression of Recombinant HA in Insect Cells

The chimeric recombination plasmids containing cloned HA genes were purified and 2 μg was mixed with 1 μg AcNPV wild type DNA. The DNAs were co-precipitated with calcium and transfected into *S. frugiperda* cells using standard procedures (Smith, Summers, and Fraser, *Mol. and Cell. Biol.* 3:2156–2165 (1983)). Recombinant baculoviruses were identified on the basis of plaque morphology then further purified by additional rounds of plaque-purification. Plaque-purified recombinant baculoviruses are screened for expression of rHA and a single baculovirus expression vector was selected for further development.

*S. frugiperda* cells were infected with a baculovirus vector containing the HA gene from the Influenza strain: B/Panama/45/90. At 24, 48, and 72 hours post infection, $1\times10^6$ cells were pulsed with 25 μCi [$^{35}$S]methionine for 15 minutes to label proteins being synthesized. The cells were collected and the proteins separated on an 11% polyacrylamide gel in the presence of 0.1% SDS. The radiolabeled proteins were detected by exposure to X-OMAT-AR film. The location of protein standards and their size in kilodaltons (kd) indicated that the 85 kd recombinant HA protein is one of the major proteins being synthesized in the cells at 48 hours and 72 hours post infection.

EXAMPLE 5

Production and Purification of Recombinant HA

The baculovirus expression vector A8611, which contains the gene for influenza A/Beijing/353/89, produced essentially as described above for A/Beijing/32/92 hemagglutinin under the control of the polyhedrin promoter, was used to infect *S. frugiperda* cells. Cells were grown at 27° C. to a density of $1\times10^6$ cells/mL in TNMFH media (Gibco BRL, Gaithersburg, Md.) supplemented with 10% fetal bovine serum, and infected at a multiplicity of infection (MOI) of 1 with the A8611 recombinant baculovirus. During infection the influenza A/Beijing/353/89 hemagglutinin is produced under the transcriptional control of the baculovirus polyhedrin promoter. Cells are harvested 72 hours post-infection by centrifugation for 15 minutes at 3,400 x g, and washed by resuspension in serum-free TNMFH media followed by centrifugation for 30 minutes at 10,400 x g. The supernatant is decanted, and infected cell pellets are stored at −70° C.

A process was developed in which the recombinant HA is selectively extracted from the infected cells under conditions that do not denature the antigen. Unless noted, all extraction steps are performed at 4° C. The cell pellet from 0.5 L of culture (approximately $5\times10^8$ cells) was disrupted for 2 minutes in 40 mL of ice-cold 30 mM Tris-HCl, pH 8.4, 25 mM LiCl, 1% (v/v) TWEEN-20™, 1 mg/mL leupeptin, using a POLYTRON™ homogenizer (Brinkmann Instruments Inc. Westbury, N.Y.). The homogenate was centrifuged for 30 minutes at 9,200 x g. The supernatant was discarded, and the pellet collected. This step removes soluble and peripheral membrane proteins from the insect cells without extraction of integral membrane proteins like rHA. To extract the rHA the pellet was homogenized for 2 minutes at a setting of 4 in 40 mL of ice-cold 30 mM Tris, 10 mM ethanolamine, pH 11, 25 mM LiCl, 2% TWEEN-20™. After a 60 minute incubation on ice, the pH of the homogenate was adjusted to 8.4 with 1N HCl, and insoluble material was removed by centrifugation for 30 minutes at 9,200 x g. The supernatant containing the soluble rHA was decanted, and the pH was checked and, if necessary, adjusted to 8.4 at room temperature. The insoluble material was resuspended in 40 mL of water for analysis. The HA integral membrane protein was solubilized under the high pH, Tween-20 polyoxyethlene (20) sorbitan monolaurate (TWEEN-20™ a detergent) conditions and remains in solution after the pH is dropped.

Proteins were analyzed by SDS polyacrylamide gel electrophoresis. Samples were disrupted in a boiling water bath for 10 minutes in the presence of 2% sodium dodecyl sulfate (SDS) and 5% beta-mercaptoethanol, then electrophoresed on an 11% polyacrylamide gel in the presence of 0.1% SDS, then stained with Coomassie blue.

A chromatography purification process was developed to purify recombinant HA which results in a highly purified recombinant HA antigen that is non-denatured and suitable as a component of an influenza vaccine for human use. The following procedure was used to purify the A/Beijing/353/89 HA from *S. frugiperda* cells infected with the recombinant virus A8611.

The chromatography gel matrices used to purify HA from 0.5 L of infected *S. frugiperda* cells were 30 mL Pharmacia DEAE Sepharose Fast Flow (in a Pharmacia C16/20 column) and a 4 mL Pharmacia Lentil Lectin Sepharose 4B (in a Pharmacia C10/10 column). The outlet of the DEAE column is connected to the inlet of the lentil lectin column, and the S/N 2 cell extract prepared as described above was applied to the coupled columns at a flow rate of 1 mL/minute. The columns were washed with 30 mM Tris-HCl, pH 8.4, 25 mM LiCl, 0.5% TWEEN-20™ until the UV absorption at 280 nm of the lentil lectin effluent returns to baseline. Under these conditions most of the contaminating proteins bind to DEAE but recombinant HA flows through the column. The remaining contaminants pass through the lectin column and glycosylated rHA binds to the lentil lectin affinity matrix. The DEAE column is disconnected, and the lectin column is washed with another 40 mL of 30 mM Tris-HCl, pH 8.4, 25 mM LiCl, 0.5% Tween-20. Next, the lectin column is washed with 40 mL of 30 mM Tris-HCl, pH 8.4, 25 mM LiCl, 0.4% (v/v) sodium deoxycholate (DOC). This step replaces the polyoxyethlene (20) sorbitan monolaurate (TWEEN-20™, a detergent) with a detergent, like DOC, that can be removed from the protein by dialysis. Recombinant HA is then eluted from the lectin column with approximately 20 mL of 40 mL of 30 mM Tris-HCl, pH 8.4, 25 MM LiCl, 0.4% (v/v) sodium deoxycholate containing 0.3M a-D-methyl mannoside. Results are analyzed by 11% PAGE.

Due to the genetic variability of influenza HA proteins, the details of the above purification process may vary with each unique recombinant HA protein. For example, the rHA may bind to the DEAE ion exchange column instead of flowing through. Should this occur, the rHA would be removed from the DEAE column with by washing the column with buffer containing higher concentration of LiCl, NaCl, or other salts.

To remove the DOC detergent and other buffer components, the eluate from the lectin column containing the purified rHA was dialyzed against phosphate buffered saline, pH 7.5 (PBS). The purified recombinant HA was at least 95% pure as determined by analysis on SDS polyacrylamide gels.

EXAMPLE 6

Analysis of rHA Protease Resistance

Mature HA assembles into trimeric structures which are resistant to a variety of proteases, including trypsin, that degrade HA monomers (Murphy and Webster, 1990). Resistance to trypsin treatment can therefore be used as an assay for functional trimer formation. The following procedure was used to study resistance of rHA to protease treatment.

Two aliquots of purified rHA (A/Beijing/353/89) at 60 μg/mL were incubated on ice for 30 minutes in 30 mM Tris-HCl, pH 8.4, 150 mM NaCl, in the presence and absence of 50 μg/mL TPCK-treated trypsin. The reaction was stopped by the addition of 57.4 mM phenyl methyl sulfonyl fluoride in isopropanol to a final concentration of 1 mM. Aliquots of each sample were denatured by boiling in 3% SDS under reducing conditions, electrophoresed on 11.5% polyacrylamide gels, and transferred to nitrocellulose filter using standard Western blotting procedures. The HA polypeptides were detected using guinea pig anti-HA serum prepared against purified rHA and a goat anti-guinea pig IgG alkaline phosphatase conjugate.

Untreated rHA migrates at the size of the HA precursor (HA0). Protease treatment results in two major bands that migrate at the sizes predicted for influenza hemagglutinin HA1 and HA2. The results show that trypsin cleaves the rHA protein once to produce two polypeptides that are the sizes predicted for HA1 and HA2. No further proteolytic processing occurs. These results demonstrate that rHA purified by the above process is resistant to degradation by protease. This property is consistent with purified rHA being in the form of trimers.

EXAMPLE 7

Immunogenicity of rHA Using Standardized Mouse Potency Assay

One approach to measure immunogenicity of an antigen is to determine the quantity necessary to induce a detectable antibody response in mice (mouse potency assay). A standardized mouse potency assay is used to measure the immunogenicity of rHA0 vaccine. Groups of 5–10 mice are immunized once with vaccine containing serial dilutions of rHA, i.e., 0.500 μg, 0.1 μg, 0.02 μg, and 0.004 μg purified rHA. Sera are collected 28 days post immunization and antibodies against the rHA antigen measured in a standard enzyme-linked immunological solid-phase assay (ELISA) in 96 well microtiter plates. A mouse has seroconverted if the OD450 at a 1:100 dilution of the 28 day antisera is greater than three standard deviations above the mean of the OD450 of mouse pre-immune sera. The effective dosage of vaccine needed to seroconvert 50% of the mice (ED50) is a measure of the immunogenicity of the antigen.

For example, four groups of 10 mice are immunized once with either 0.1 μg, 0.02 μg, 0.004 μg, or 0.0008 μg (5-fold dilutions) of rHA0 vaccine. Sera are collected 28 days post immunization and measured against each rHA0 antigen in the vaccine for seroconversion in an ELISA assay. The dosage needed to seroconvert 50% of the mice ($ED_{50}$) is calculated and a minimum $ED_{50}$ established for each rHA0 antigen.

Preliminary data shows that a single dose of 0.004 μg of rHA0 will seroconvert at least 50% of the mice.

EXAMPLE 8

Administration of rHA in Combination with an Adjuvant and Comparison with Available Influenza Vaccines The mouse potency of purified rHA from influenza A/Beijing/353/89 was tested with alum or without alum (neat) and compared to a commercial influenza vaccine, FLUZONE® flu vaccine (Connaught Laboratories, Inc. Swiftwater, Pa.) which contains the A/Beijing/353/89 strain of influenza. Vaccine was administered in a dosage of 0.5 μg, 0.1 μg, 0.02 μg, and 0.04 μg. The mice were boosted at day 28 with the doses of purified rHA described above. On day 42 sera were collected and titered in an ELISA assay for IgG anti-HA antibodies.

Figure 3:
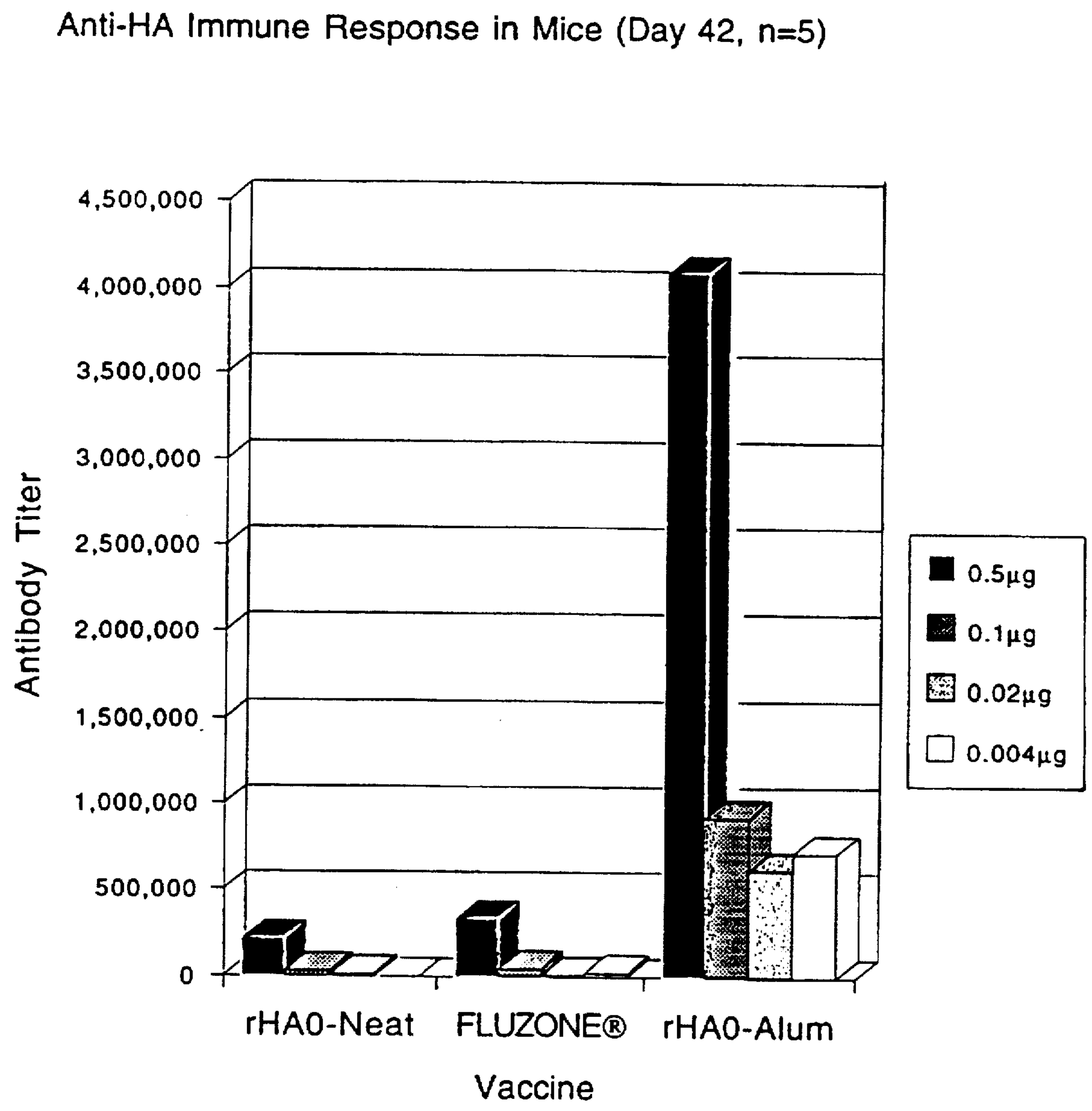
FIG. 3 is a graph of the anti-HA immune response in mice, day 42, n=5, graphing antibody titer for rHA0-neat; Fluzone® (licensed trivalent subvirion vaccine containing 15 μg/dose of each the HAs from influenza A/Texas/36/91 $N_1N_1$), A/Beijing/32/92 ($H_3N_2$) and B/Panama, 45/90 viruses, i.e., 45 μg HA/ 0.5 mL dose; Connaught Laboratories, Inc., Swiftwater, Pa.) vaccine, and rHA0-alum, at dosages of 0.5 μg (dark bars), 0.1 μg (shaded bars), 0.02 μg (dotted bars), and 0.004 μg (open bars).

The results are shown in FIG. 3. In the absence of adjuvant, only a dosage of 0.5 μg induced production of significant antibody titer (200,000). In the presence of adjuvant, dosages of as little as 0.004 μg of rHA0 produced significant antibody. The animals immunized with rHA (neat) produced approximately the same levels of anti-HA antibodies as the commercial vaccine. Alum increased the immunogenicity of rHA, and anti-HA titers were generated that were 10-fold or higher than without adjuvant.

In summary, comparison of the immunogenicity of purified rHA0s with an influenza whole virion vaccine, (FLUZONE®, flu vaccine, Connaught Laboratories, Inc., Swiftwater, Pa.), demonstrates that rHA0 elicits a similar immune response in mice over a period of 42 days. Adsorption of the rHA0 to alum significantly increases the immunogenicity of the purified rHA0 in mice, as measured by the assay described in Example 7. The combination with alum elicits IgG hemagglutinin antibodies that are higher than the FLUZONE® flu vaccine influenza vaccines.

EXAMPLE 9

Hemagglutination Inhibition Studies

Hemagglutination inhibition (HAI) antibodies bind to three of four known epitopes on hemagglutinin and block the ability of influenza to agglutinate red blood cells (Wilson et al, "Structure of the hemagglutinin membrane glycoprotein of influenza virus at 3A° resolution". *Nature*, 289:366–378 (1981)). These antigenic determinants are clustered around the sialic acid receptor binding site on hemagglutinin trimers. Antibodies against these sites will neutralize virus infectivity (Weis, et al., "Structure of the influenza virus hemagglutinin complexed with its receptor, sialic acid". *Nature* 333:426–431 (1988)). The titer and specificity of HAI antibodies are an important measure of the potential for an influenza vaccine to protect against infection with like and related strains of influenza.

Studies were conducted in mice comparing the ability of purified rHA0 from A/Beijing/353/89 and FLUZONE® vaccine (Connaught Laboratories, Inc., Swiftwater, Pa.) to elicit HAI antibodies. Groups of 5 mice were injected on days 0 and 28 with 0.5 μg, 0.1 μg, 0.02 μg, or 0.004 μg of rHA0 or three times these quantities of FLUZONE® vaccine hemagglutinin so that equal levels of recombinant or viral A/Beijing/353/89 hemagglutinin were administered. For example, mice in the highest dose group were immunized with 1.5 μg of FLUZONE® vaccine hemagglutinin (0.5 μg of hemagglutinin from each strain) and 0.5 μg rHA0. The presence of additional hemagglutinin antigen in FLUZONE® vaccine from two other influenza strains may result in some cross-reactive antibodies.

Anti-hemagglutinin antibodies (hemagglutinin IgG) were measured in a standard dilutional ELISA against purified rHA0. HAI antibodies were measured against 4 hemagglutinin units of the following antigens: whole influenza A/Beijing/353/89 virus (A/Bei), purified rHA0 A/Beijing/353/89 antigen, and FLUZONE® flu vaccine. The HAI titer is the reciprocal of the highest dilution of antisera which inhibits the agglutination of chicken red blood cells by 50%.

Table 3 summarizes serum hemagglutinin IgG and HAI titers in the mice at day 42. High levels of anti-hemagglutinin antibodies were produced with the recombinant rHA0 vaccine. These were about ten fold higher titers than FLUZONE® flu vaccine. Most significant is that the rHA0 vaccine produced good titers of antibodies that block agglutination of red blood cells by the A/Beijing/353/89 virus and rHA0 antigens. Thus, the rHA0 vaccine produced HAI antibodies that recognized equally well the immunogen and the influenza A/Beijing virus. The lower HAI titers against FLUZONE® flu vaccine may be due to the inability of the antisera to block agglutination by the other two strains of hemagglutinin in the FLUZONE® vaccine. In contrast, FLUZONE® vaccine immunized mice produce high HAI antibodies when measured only against itself. The HAI titers against influenza A/Beijing/353/89 virus and the rHA0 antigen were considerably reduced. Similar patterns were observed in the mice in the lower dose groups.

TABLE 3

HAI Titers against rHA0 and FLUZONE ® vaccine

| | rHA0 A/Bei (day 42) | | | | FLUZONE ® (day 42) | | | |
|---|---|---|---|---|---|---|---|---|
| | HA IgG | HAI | | | HA IgG | HAI | | |
| Mouse # | rHA0 | A/Bei | rHA0 | FLUZONE ® vaccine | rHA0 | A/Bei | rHA0 | FLUZONE ® vaccine |
| 1 | 4,096,000 | 1,920 | 960 | 15 | 256,000 | <10 | <10 | 600 |
| 2 | 4,096,000 | 480 | 480 | 15 | 512,000 | 120 | 120 | 600 |
| 3 | 8,192,000 | 1,920 | 960 | 15 | 256,000 | 60 | 60 | 300 |
| 4 | 4,096,000 | 960 | 960 | 30 | 128,000 | 30 | 30 | 400 |
| 5 | 4,096,000 | 1,920 | 960 | 60 | 512,000 | 80 | 80 | 400 |
| MEAN | 4,915,000 | 1,440 | 864 | 27 | 332,800 | 58 | 58 | 460 |

These data also suggest that there are genetic differences between the influenza A/Beijing/353/89 strain in FLUZONE® flu vaccine and this same strain of influenza obtained from the FDA and passaged once in eggs prior to using the HAI assay. The fact that antibodies produced in response to the recombinant HA0 cloned from influenza A/Beijing/353/89 blocks agglutination of red blood cells by this strain of influenza as well as itself is good evidence that there were no genetic changes during the cloning process that effected the sialic acid receptor binding site on the purified rHA0 antigen.

EXAMPLE 10

Formulation of a 1993/1994 Influenza Vaccine

Equal concentrations of purified rHA0 antigens from the three FDA recommended 1993/94 strains of influenza will be combined into a single dose in glass vials, at 0.5 mL volume per dose, in the absence of preservative, in a phosphate buffered saline solution, with and without alum.

Initially, a trial will be conducted in healthy adults immunized with escalating doses of a recombinant trivalent hemagglutinin influenza vaccine to establish safety, immunogenicity, and dosing information. A blinded, placebo controlled trial will follow several months later with a larger number of individuals to confirm safety and immunogenicity and provide preliminary efficacy data.

In the first study, groups of ten subjects will receive escalating doses of a trivalent recombinant rHA0 influenza vaccine or a licensed 1993/94 hemagglutinin split vaccine, as shown in Table 4:

TABLE 4

Administration of Vaccine to humans to determine safety.

| Group | Subjects | Vaccine/Placebo |
|---|---|---|
| 1 | 10 | 15 μg rHA0 |
| 2 | 10 | 45 μg rHA0 |
| 3 | 10 | 135 μg rHA0 |
| 4 | 10 | 45 μg licensed influenza vaccine |

Forty volunteers will be randomized into one of 4 groups of 10 subjects. Sequential groups of 10 subjects will receive 15 μg, 45 μg, or 135 μg doses of rHA0 vaccine by intramuscular injection. Volunteers in groups 1, 2, and 3 will be enrolled at 1-week intervals to allow clinical and laboratory assessment of the toxicity of each dose prior to vaccination with the next higher dose. Subjects in group 4 will be immunized with a licensed influenza vaccine.

Vaccine safety will be evaluated for an increase of 4-fold or more in IgG serum hemagglutinin antibody titer; an increase of 4-fold or more in serum hemagglutinin inhibition antibody; an increase of 4-fold or more in serum neutralizing antibody; and an increase of 4-fold or more in lymphoproliferative responses.

In a second group of studies, groups of 200–300 subjects will be randomized to be immunized with the recombinant trivalent 1993/94 rHA0 vaccine or a licensed 1993/94 influenza vaccine. Subjects will be followed for immunological and virological signs of infection and disease, as shown in Table 5:

TABLE 5

Administration of Vaccine to humans to determine efficacy.

| Group | Subjects | Vaccine/Placebo |
|---|---|---|
| 1 | 200–300 | Recombinant HA0 vaccine |
| 2 | 200–300 | Licensed influenza vaccine |

400–600 healthy adult subjects will be enrolled in a two arm trial with 200–300 volunteers per group. The volunteers will be randomized to receive recombinant HA0 vaccine or a licensed influenza vaccine. Subjects will be monitored weekly for approximately six months for safety, immunogenicity, infection, and clinical symptoms.

Safety, immunogenicity and efficacy will be determined by measuring infection frequencies as a function of the presence of virus in nasal-wash specimens titered on MDCK cells and overall clinical illness score based on measurements of oral temperature, signs of upper or lower respiratory infection, and myalgias.

Modifications and variations of the methods and compositions described herein for use in preparing and using a recombinant influenza vaccine will be obvious to those skilled in the art. Such modifications and variations are intended to come within the scope of the appended claims.

We claim:

1. Substantially pure, recombinant, mature, glycosylated influenza hemagglutinin produced by a baculovirus expression system in cultured insect cells, wherein said hemagglutinin protein is purified to 95% or greater and said protein is immunogenic, and induces a protective immune response when used as a vaccine.

2. A vaccine composition comprising the protein of claim 1, and a pharmaceutically acceptable carrier.

3. A vaccine composition comprising the protein of claim 1, and an adjuvant and a pharmaceutically acceptable carrier.

4. The vaccine composition of claim 2 wherein the pharmaceutically acceptable carrier is a polymeric delivery system.

5. The protein of claim 1 wherein the influenza is selected from the group consisting of influenza A strains and influenza B strains.

6. A method for vaccinating an animal against influenza comprising administering to the animal an effective amount of the protein of claim 1.

7. The method of claim 6 further comprising administering the protein in combination with an adjuvant.

8. The method of claim 6 further comprising administering the protein in a polymeric delivery system.

9. The method of claim 6 wherein the influenza is selected from the group consisting of influenza A strains and influenza B strains.

10. The method of claim 6 wherein the animal is selected from the group consisting of a mammal and an avian species.

11. The method of claim 6 wherein the animal is a human.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Influenza virus ( x ) PUBLICATION INFORMATION:
( A ) AUTHORS: Davis, et al.
( B ) TITLE:Construction and Characterization of a Bacterial Clone Containing the Hemagglutinin Gene of the WSN Strain (HON1) of Influenza Virus
( C ) JOURNAL: Gene
( D ) VOLUME: 10
( F ) PAGES: 205-218
( G ) DATE: 1980

( x i ) SEQUENCE DESCRIPTION: SEQ ID NO:1:

AGCAAAAGCA GG 12

( 2 ) INFORMATION FOR SEQ ID NO:2:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GGGGGTACCC CCGGGAGCAA AAGCAGGGGA AAATAAAAA 39

( 2 ) INFORMATION FOR SEQ ID NO:3:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

CCCGGTACCT CAKATKCATA TTCTGCACTG CAAAG 35

( 2 ) INFORMATION FOR SEQ ID NO:4:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

-continued ( x i ) SEQUENCE DESCRIPTION: SEQ ID NO:4:

GGGGGTACCC CCGGGGACAC AATATGTATA GGCTACCAT 39

( 2 ) INFORMATION FOR SEQ ID NO:5:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

GGGGGATCCG GTACCAGCAA AAGCAGGGGA TAATTCTAT 39

( 2 ) INFORMATION FOR SEQ ID NO:6:

( i ) SEQUENCE CHARACTERISTICS:
( A ) LENGTH: 1030 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Influenza virus ( x i ) SEQUENCE DESCRIPTION: SEQ ID NO:6:

TAATAAAAAA ACCATAAATA ATGCCCTTGT ACAAATTGTT AAACGTCTGG TGGTTGGTCG 60
CCGTTTCTAA CGCGATTATT TTTTTGGTAT TTATTACGGG AACATGTTTA ACAATTTGCA 120
GACCACCAAC CAGCGGCAAA GATTGCGCCA AAAACTNCCC GGAATTGANA ANAGNACAGA 180
AACGCTGTGC CTGGGANATC ATGNAGTGCC AAACGGAACG NTAGTGGTTT TTGANGGGCC 240
TTAACTNTTN TCNTGTCTTT GCGACACGGA CCCTNTAGTA CNTCACGGTT TGCCTTGCNA 300
TCACAAAANA ATCACGANTG ANCAATTNGA GGTGANTAAT GNTACTGAGC TGGTNCAGAG 360
TCCCNCAANA GGTNGANTTT GNTTTTNTTA GTGCTNACTN GTTAANCTCC ACTNATTACN 420
ATGACTCGAC CANGTCTCAG GGNGTTNTCC ANCTNAAACN GANAGTCCNC ACCGANTCCT 480
NGNTGGAAAA AACTGNACAC TGATNGATGC TCTTTTGGGA GACCCNCATN GTGATGGTCT 540
NTCAGGNGTG GCTNAGGANC NACCTTTTTT GACNTGTGAC TANCTACGAG AAAACCCTCT 600
GGGNGTANCA CTACCATTCC ANAATAAGGA NTGGNACCTT TTGGNNGANC GCAGCAAAGC 660
TTACAGAAAC TGTTACCCTT ATGATGTNCC GGNTAAGGTN TTATTCCTNA CCNTGGAAAA 720
CCNNCTNGCG TCGTTTCGAA TGTCTTTGAC AATGGGAATA CTACANGGCC NANATGCCNC 780
CCTTAGGTCA CTAGTTGCCN CATCAGGNAC CCTGGNGTTT TNTCAATGAA GANTCCAATT 840
GGCTTGGAGT NTACGGNGGG AATCCAGTGA TCAACGGNGT AGTCCNTGGG ACCNCAAAAN 900
AGTTACTTCT NAGGTTAACC GAACCTCACN GTCCAGNATG GGGGAAGGTT TTNTTGGAAA 960
AGGGGNTTTT TCAAAAGTTG NCAGGTCNTA CCCCCTTCCA AAANAACCTT TTCCCCNAAA 1020
AAGTTTTCAA 1030

( 2 ) INFORMATION FOR SEQ ID NO:7:

( i ) SEQUENCE CHARACTERISTICS:

-continued ( A ) LENGTH: 165 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Influenza virus ( x i ) SEQUENCE DESCRIPTION: SEQ ID NO:7:

Met Pro Leu Tyr Lys Leu Leu Asn Val Trp Trp Leu Val Ala Val Ser
1 5 10 15

Asn Ala Gln Lys Leu Pro Gly Ile Xaa Xaa Xaa Thr Glu Thr Leu Cys
20 25 30

Leu Gly Xaa His Xaa Val Pro Asn Gly Thr Xaa Val Lys Xaa Ile Thr
35 40 45

Xaa Xaa Gln Xaa Glu Val Xaa Asn Xaa Thr Glu Leu Val Gln Ser Pro
50 55 60

Xaa Xaa Gly Xaa Xaa Xaa Xaa Ser Pro His Arg Xaa Leu Xaa Gly Lys
65 70 75 80

Asn Xaa Thr Leu Xaa Asp Ala Leu Leu Gly Asp Pro His Xaa Asp Gly
85 90 95

Phe Xaa Asn Lys Xaa Trp Xaa Leu Leu Xaa Xaa Arg Ser Lys Ala Tyr
100 105 110

Arg Asn Cys Tyr Pro Tyr Asp Val Pro Xaa Xaa Ala Xaa Leu Arg Ser
115 120 125

Leu Val Ala Xaa Ser Gly Thr Leu Xaa Phe Xaa Gln Xaa Arg Xaa Gln
130 135 140

Leu Ala Trp Ser Xaa Ser Xaa Met Gly Glu Gly Phe Xaa Gly Lys Gly
145 150 155 160

Xaa Phe Ser Lys Val
165

( 2 ) INFORMATION FOR SEQ ID NO:8:

( i ) SEQUENCE CHARACTERISTICS:
( A ) LENGTH: 1030 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Influenza virus ( x i ) SEQUENCE DESCRIPTION: SEQ ID NO:8:

TAATAAAAAA ACCATAAATA ATGCCCTTGT ACAAATTGTT AAACGTCTGG TGGTTGGTCG 60

CCGTTTCTAA CGCGATTATT TTTTTGGTAT TTATTACGGG AACATGTTTA ACAATTTGCA 120

GACCACCAAC CAGCGGCAAA GATTGCGCGA CACAATATGT ATAGGCTACC ATGCNANCAA 180

CTCAACCGAC ACTGTTGACA CAGTACTTGA GAAGAACGTG ACAGTGCTGT GTTATACATA 240

TCCGATGGTA CGNTNGTTGA GTTGGCTGTG ACAACTGTGT CATGAACTCT TCTTGCACTG 300

-continued

```
TCACACACAC TCTGTCAACC TACTTGAGGA CAGTCACANC GGAAAACTAT GTCGACTAAA  360

GGGAATAGCC CCACTACAAT TGTGTGTGAG ACAGTTGGAT GAACTCCTGT CAGTGTNGCC  420

TTTTGATACA GCTGATTTCC CTTATCGGGG TGATGTTAAC GGTAATGGNA GCGTTGNCGG  480

ATGGATCTTA GGAAACCCAA AATGCGAATC ACTGTTTTCT TAGGAATCAT GGTCCTACCC  540

ATTACCNTCG CAACNGCCTA CCTAGAATCC TTTGGGTTTT ACGCTTAGTG ACAAAAGAAT  600

CCTTAGTACC AGGATGATTG CAGNAACACC AAACCCTGAG AATGGAACAT GTTACCCAGG  660

GTATTTCGCC CGACTTATGA GGAACTTGAG GGAGTAACGT CNTTGTGGTT TGGGACTCTT  720

ACCTTGTACA ATGGGTCCCA TAAAGCGGGC TGAATACTCC TTGAACTCCC TCCAATTGGA  780

GTTCAAGTNT CATCAATTCC GNGAGGATTC CGGAATTTTT CCCCCAANGA AAGTTCAATG  840

GCCCCNCCCC GTTAACCTCA AGTTCANAGT AGTTAAGGCN CTCCTAAGGC CTTAAAAAGG  900

GGGTTNCTTT CAAGTTACCG GGGNGGGGNC CCCNGNCCCA NGGGGNTNCG GGGNTCCCAA  960

TTTCTCCCCC NTTTGGGAAN GGGGNCNGGG TNCCCCNANG CCCCNAGGGT TAAAGAGGGG 1020

GNAAACCCTT                                                        1030
```

( 2 ) INFORMATION FOR SEQ ID NO:9:

( i ) SEQUENCE CHARACTERISTICS:
( A ) LENGTH: 165 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Influenza virus ( x i ) SEQUENCE DESCRIPTION: SEQ ID NO:9:

```
Met Pro Leu Tyr Lys Leu Leu Asn Val Trp Trp Leu Val Ala Val Ser
1               5                   10                  15

Asn Ala Asp Thr Ile Cys Ile Gly Tyr His Ala Xaa Asn Ser Thr Asp
            20                  25                  30

Thr Val Asp Thr Val Leu Glu Lys Asn Val Thr Val Thr His Ser Val
        35                  40                  45

Asn Leu Leu Glu Asp Ser His Xaa Gly Lys Leu Cys Arg Leu Lys Gly
    50                  55                  60

Ile Ala Pro Leu Gln Leu Gly Asn Gly Ser Val Xaa Gly Trp Ile Leu
65                  70                  75                  80

Gly Asn Pro Lys Cys Glu Ser Leu Phe Ser Xaa Glu Ser Trp Ser Tyr
                85                  90                  95

Ile Ala Xaa Thr Pro Asn Pro Glu Asn Gly Thr Cys Tyr Pro Gly Tyr
            100                 105                 110

Phe Ala Arg Leu Met Arg Asn Leu Arg Glu Gln Leu Glu Phe Lys Xaa
        115                 120                 125

His Gln Phe Arg Glu Asp Ser Gly Ile Phe Pro Pro Xaa Lys Val Gln
    130                 135                 140

Trp Pro Xaa Pro Xaa Pro Xaa Pro Xaa Gly Xaa Gly Xaa Pro Asn Phe
145                 150                 155                 160

Ser Pro Xaa Trp Glu
```

-continued

165

( 2 ) INFORMATION FOR SEQ ID NO:10:

( i ) SEQUENCE CHARACTERISTICS:
( A ) LENGTH: 874 base pairs
( B ) TYPE: nucleic acid
( C ) STRANDEDNESS: single
( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
( A ) ORGANISM: Influenza virus ( x i ) SEQUENCE DESCRIPTION: SEQ ID NO:10:

```
TAATAAAAAA ACCATAAATA ATGCCCTTGT ACAAATTGTT AAACGTCTGG TGGTTGGTCG   60
CCGTTTCTAA CGCGATTATT TTTTTGGTAT TTATTACGGG AACATGTTTA ACAATTTGCA  120
GACCACCAAC CAGCGGCAAA GATTGCGCTC TTCAAACTCA CCTCATGTGG TCAAAACAGC  180
TACTCAAGGG GAAGTCAATG TGACTGGTGT GATACCACTG ACAACAAGAA GTTTGAGTGG  240
AGTACACCAG TTTTGTCGAT GAGTTCCCCT TCAGTTACAC TGACCACACT ATGGTGACTG  300
TTGTACACCA ACAAAATCTC ATTTNGNAAA TCTAAAAGGA ACAAAGACCA GAGGGAAACT  360
ATGCCCAAAC TGTCTCAACT GCTGTGGTTG TTTTAGAGTA AANCNTTTAG ATTTTCCTTG  420
TTTCTGGTCT CCCTTTGATA CGGGTTTGAC AGAGTTGACG ACAGATCTGG ATGTGGCCTT  480
GGGCAGACCA ATGTGTGTGG GGACCACACC TTCGGCAAAA GCTTCAATAC TCCACGAATG  540
TCTAGACCTA CACCGGAACC CGTCTGGTTA CACACACCCC TGGTGTGGAA GCCGTTTTCG  600
AAGTTATGAG GTGCTTGTCA GACCTGTTAC ATCCGGGTGC TTTCCTATNN TGCACGACAG  660
GACAAAANTC AGACAGGTAC CCANTCTTCT CAGACAGTCT GGACAATGTA GGCCCACGAA  720
AGGATANNAC GTGCTGTCCT GTTTTNAGTC TGTCCATGGG TNAGAAGAGT CTGGNTNTGA  780
AATNTCAGAT TATCAACCCC AANCGTTATC AANGAGGGNG GGGCCNANAC TTTANAGTCT  840
AATAGTTGGG GTTNGCAATA GTTNCTCCCN CCCC                              874
```

( 2 ) INFORMATION FOR SEQ ID NO:11:

( i ) SEQUENCE CHARACTERISTICS:
( A ) LENGTH: 139 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Influenza virus ( x i ) SEQUENCE DESCRIPTION: SEQ ID NO:11:

```
Met Pro Leu Tyr Lys Leu Leu Asn Val Trp Trp Leu Val Ala Val Ser
1               5                   10                  15

Asn Ala Ser Ser Asn Ser Pro His Val Val Lys Thr Ala Thr Gln Gly
            20                  25                  30
```

-continued

| | | | | | | | | | | | | | | | |
|---|---|---|---|---|---|---|---|---|---|---|---|---|---|---|---|
| Glu | Val | Asn 35 | Val | Thr | Gly | Val | Ile 40 | Pro | Leu | Thr | Thr | Thr 45 | Pro | Thr | Lys |
| Ser | His 50 | Xaa | Xaa | Asn | Leu | Lys 55 | Gly | Thr | Lys | Thr | Arg 60 | Gly | Lys | Leu | Cys |
| Pro 65 | Asn | Cys | Leu | Asn | Cys 70 | Thr | Asp | Leu | Asp | Val 75 | Ala | Leu | Gly | Arg | Pro 80 |
| Met | Cys | Val | Gly | Thr 85 | Thr | Pro | Ser | Ala | Lys 90 | Ala | Ser | Ile | Leu | His 95 | Glu |
| Val | Arg | Pro | Val 100 | Thr | Ser | Gly | Cys | Phe 105 | Pro | Xaa | Xaa | His | Asp 110 | Arg | Thr |
| Lys | Xaa | Arg 115 | Gln | Val | Pro | Xaa | Leu 120 | Leu | Arg | Gly | Xaa | Glu 125 | Xaa | Ser | Asp |
| Tyr | Gln 130 | Pro | Gln | Xaa | Leu | Ser 135 | Xaa | Arg | Xaa | Gly | | | | | |

( 2 ) INFORMATION FOR SEQ ID NO:12:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:12:

GGGGGTACCC CCGGGGACTT TCCAGGAAAT GACAACAG 38

( 2 ) INFORMATION FOR SEQ ID NO:13:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( x i ) SEQUENCE DESCRIPTION: SEQ ID NO:13:

CCCGGTACCG AATCATCCTA GAAACAAGGG TGTTTTTAAT TAAT 44

( 2 ) INFORMATION FOR SEQ ID NO:14:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( x i ) SEQUENCE DESCRIPTION: SEQ ID NO:14:

GGGGAATTCG GTACCCCCGG GAAGGCAATA ATTGTACTAC TCATGGT 47

( 2 ) INFORMATION FOR SEQ ID NO:15:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:15:

GGTACCCCCG GGGATCGAAT CTGCACTGGG ATAACA 36

( 2 ) INFORMATION FOR SEQ ID NO:16:

( i ) SEQUENCE CHARACTERISTICS:
( A ) LENGTH: 50 base pairs
( B ) TYPE: nucleic acid
( C ) STRANDEDNESS: single -continued ( D ) TOPOLOGY: linear ( x i ) SEQUENCE DESCRIPTION: SEQ ID NO:16:

GGGGAATTCG GATCCGGTAC CTCACAGACA GATGGARCAA GAAACATTGT 50